(12) United States Patent
Ikemoto et al.

(10) Patent No.: US 6,870,067 B2
(45) Date of Patent: Mar. 22, 2005

(54) PROCESS FOR THE SYNTHESIS OF TRIFLUOROPHENYLACETIC ACIDS

(75) Inventors: Norihiro Ikemoto, Edison, NJ (US); Spencer D. Dreher, Metuchen, NJ (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 10/680,025

(22) Filed: Oct. 7, 2003

(65) Prior Publication Data

US 2004/0077901 A1 Apr. 22, 2004

Related U.S. Application Data

(60) Provisional application No. 60/416,891, filed on Oct. 8, 2002.

(51) Int. Cl.[7] ......................... C07C 51/255; C07C 55/28

(52) U.S. Cl. ........................................ 562/408; 562/489
(58) Field of Search .................................. 562/408, 489

(56) References Cited

PUBLICATIONS

Shi et al, Crystallization–Induced Asymmetric Transformation:Stereospecific synthesis of L–768,673, 1999, 55, p. 909–918.*

* cited by examiner

*Primary Examiner*—Cecilia J. Tsang
*Assistant Examiner*—Taylor Victor Oh
(74) *Attorney, Agent, or Firm*—Philippe L. Durette; Mel Winokur

(57) ABSTRACT

The present invention is concerned with a process for the preparation of trifluorophenylacetic acids using a Grignard reagent and an allylating agent, such as allyl bromide.

10 Claims, No Drawings

PROCESS FOR THE SYNTHESIS OF TRIFLUOROPHENYLACETIC ACIDS

CROSS-REFERENCE TO RELATED APPLICATIONS

The present invention is related to U.S. provisional application Ser. No. 60/416,891, filed Oct. 8, 2002, the contents of which are hereby incorporated by reference.

BACKGROUND OF THE INVENTION

The present invention relates to processes for the preparation of trifluorophenylacetic acids useful as intermediates in the preparation of certain inhibitors of the dipeptidyl peptidase-IV ("DP-IV" or "DPP-IV") enzyme, drugs that are useful in the treatment of diabetes, and particularly type 2 diabetes. See, e.g., WO 97/40832, WO 98/19998, U.S. Pat. No. 5,939,560, Bioorg. Med. Chem. Lett., 6, 1163–1166 (1996); and Bioorg. Med. Chem. Lett., 6, 2745–2748 (1996).

Similar syntheses of phenylacetic acid derivatives from aryl halides with varying substituents have been described, e.g., in Shi, et al., Tetrahedon, 55, 908–918 (1999); U.S. Pat. No. 6,395,921; Lindley, J., Tetrahedron, 40, 1433–1456 (1984); and Setsune, et al., Chem. Ltrs., 367–370, (1981). These references describe the preparation of [bis-(trifluoromethyl)-phenyl]-acetic acids, but are not amenable to scale-up and preparation of multi-kilogram quantities. The present invention provides an effective two-step method for preparing trifluorophenylacetic acids quickly and efficiently.

In accordance with the present invention, a trifluorphenyl-Grignard reagent, i.e., magnesium-trifluorobenzene, produced from the contact of bromo-trifluorobenzene with magnesium chloride, is reacted with an allylating agent, such as allyl bromide, to form an olefin, i.e. 1-(2-propenyl)-2,4,5-trifluorobenzene, which is then oxidatively cleaved to produce the requisite trifluorophenylacetic acid. Purity and yields seen with the present process are unexpectedly high, and the two step procedure allows rapid, cost efficient and large-scale synthesis.

SUMMARY OF THE INVENTION

A process for the preparation of a compound of formula 3:

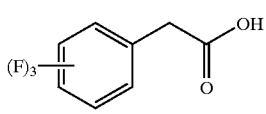

3 is disclosed comprising contacting a compound of the formula 1:

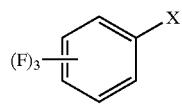

1 wherein X is a halogen selected from chlorine, bromine and iodine, with a magnesium compound and an allylating agent to produce a compound of formula 2,

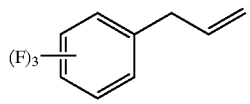

2 and reacting the compound of formula 2 with a metal catalyst and a co-oxidant to form a trifluorphenylacetic acid of formula 3.

DETAILED DESCRIPTION OF THE INVENTION

The present invention relates to processes for the preparation of trifluorophenylacetic acids. This compound is an intermediate in the synthesis of compounds that are inhibitors of the DP-IV or DPP-IV enzyme, and thus useful in the treatment of diabetes.

The invention is described herein in detail using the terms defined below unless otherwise specified.

The term "alkyl" refers to a monovalent alkane (hydrocarbon) derived radical containing from 1 to 10 carbon atoms unless otherwise defined. It may be straight, branched or cyclic. Preferred alkyl groups include methyl, ethyl, propyl, isopropyl, butyl, t-butyl, cyclopentyl and cyclohexyl.

Halogen, halide, and "halo" refer to bromine, chlorine, fluorine and iodine.

Magnesium compound refers to those magnesium containing compounds that are useful in Grignard reactions. Examples include Mg, MgCl, iPrMgCl and the like.

Allylating agent refers to a compound that reacts with a Mg containing Grignard intermediate to attach an allyl group to the phenyl ring. Examples include allyl bromide, allyl iodide and allyl chloride, with allyl bromide being preferred.

A catalyst may be useful herein, such as a metal or metal chloride, e.g., $RuCl_3$.

A co-oxidant is also typically included in the reaction. This component is useful for oxidatively cleaving the terminal carbon of the allyl group, and oxidizing the new terminal carbon to form a carboxylic acid. Examples of co-oxidants are $NaIO_4$ and $KIO_4$, with $NaIO_4$ being preferred.

The general process for the synthesis of trifluorophenylacetic acids is as follows:

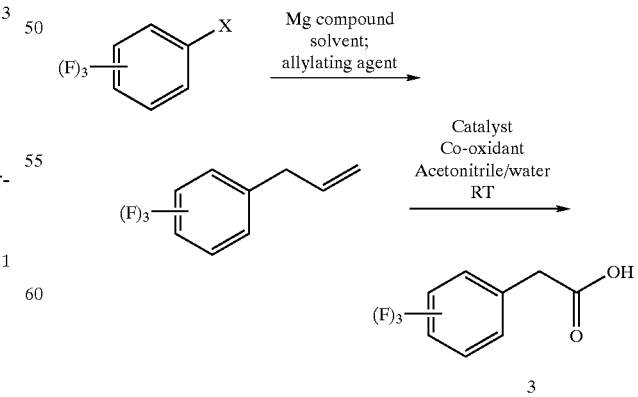

wherein X is a halide selected from bromine, chlorine and iodine.

A specific embodiment of the present invention concerns a process for the preparation of trifluorophenylacetic acids of the formula 3:

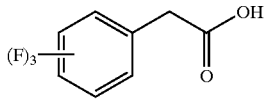

which comprises treating a reaction mixture containing isopropyl magnesium chloride and a halogenated-trifluorobenzene of the formula 1:

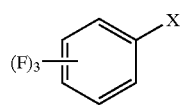

wherein X is a halide selected from bromine, chlorine and iodine, with an allylating agent such as allyl bromide to give a compound of the formula 2:

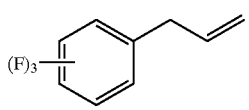

contacting the olefin with a co-oxidant and a catalyst to give a trifluorophenylacetic acid of the formula 3:

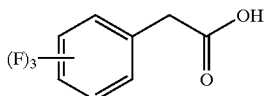

The co-oxidant is typically a periodate, such as sodium periodate or potassium periodate, which is present in combination with a metal catalyst, such as ruthenium.

A preferred embodiment of the invention relates to a process for the preparation of 2,4,5-trifluorophenylacetic acid, which comprises: (a) treating a reaction mixture comprised of isopropylmagnesium chloride and 1-bromo-2,4,5-trifluorobenzene with allyl bromide to form the olefin, 1-(2-propenyl)-2,4,5-trifluorobenzene; and
(b) reacting the 1-(2-propenyl)-2,4,5-trifluorobenzene with sodium periodate and a catalytic amount of ruthenium chloride and an aqueous solvent, to produce 2,4,5-trifluorophenylacetic acid.

The preferred ratio of allyl bromide to the starting halogenated trifluorobenzene is approximately 1:1.

Likewise, the preferred ration of magnesium chloride to bromo-trifluorobenzene is approximately 1:1.

In the current invention it is preferred that the temperature range during mixing is about −25 to about 5° C., more preferably about −12 to −14° C.

The temperature range during and following the addition of the allylating agent, e.g., allyl bromide, is about −20 to 25° C., more preferably about 5 to 20° C.

The conversion of the olefin to trifluorophenylacetic acid is preferably carried out in an aqueous environment. The preferred aqueous environment is acetonitrile and water.

The preferred metal catalyst is ruthenium chloride, and the amount of ruthenium chloride is about 0.01 to 1 equivalents, and preferably about 0.02 equivalents.

The preferred co-oxidant is sodium periodate, and the amount of sodium periodate initially added is approximately 0.5 to 1.5 equivalents, more preferably about 1 equivalent. Additional sodium periodate is charged during the reaction, approximately 3 to 4 equivalents.

The preferred temperature range during and following the addition of the metal catalyst and co-oxidant to the mixture is approximately 10–40° C., more preferably about 11 to 20 ° C.

In a highly preferred embodiment of the current invention, 1-bromo-2,4,5-trifluorobenzene is converted to its corresponding Grignard reagent with magnesium chloride in THF at about −13° C. The 2,4,5-trifluorobenzene-Grignard is then allylated by the addition of allyl bromide at about 7 to 20° C. to form the olefin, which is converted to 2,4,5-trifluorophenylacetic acid with ruthenium chloride and sodium periodate in water and acetonitrile at about 11–20° C.

None of the references cited above discuss the use of allylation and oxidation to form trifluorophenylacetic acid, in particular 2,4,5-trifluorophenylacetic acid. Furthermore, this process is more efficient, less time consuming and less costly than other processes for the production of large scale quantities.

The following examples are provided for the purpose of further illustration only and are not intended to be limitations on the disclosed invention.

The starting materials are either commercially available or known in the literature. Purification procedures include e.g., distillation, crystallization and normal or reverse phase chromatography.

EXAMPLE 1

2,4,5-Trifluorophenylacetic Acid

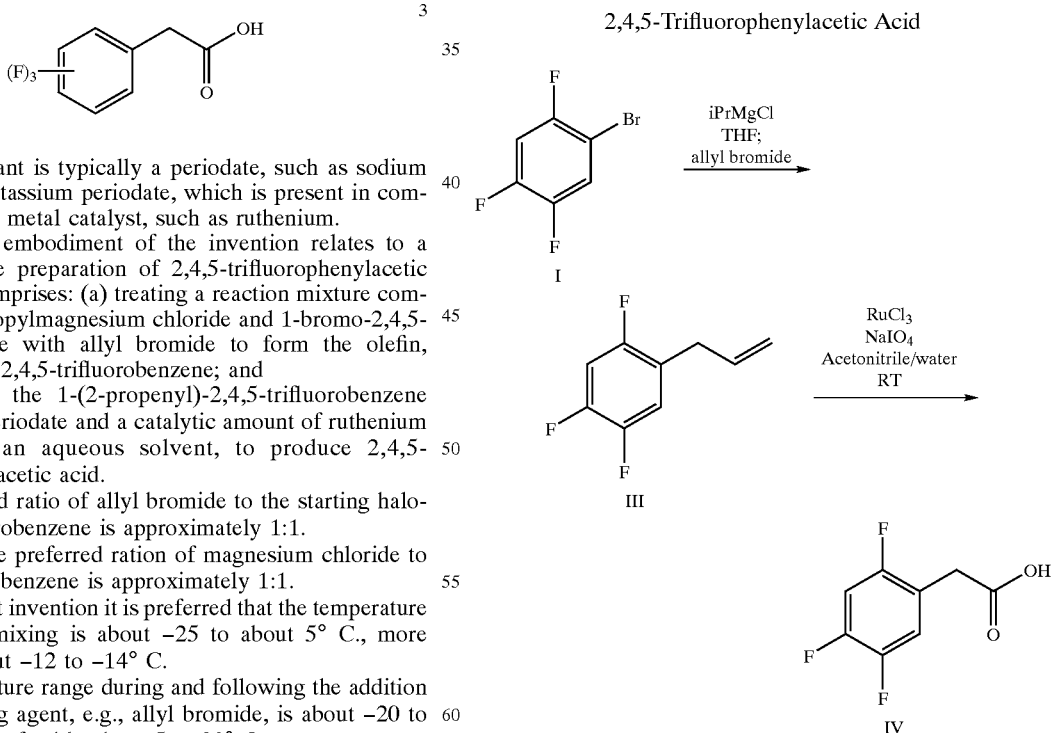

Step 1: Allylation. 1-Bromo-2,4,5-trifluorobenzene (I) was diluted in 3.55 L THF and cooled over a −15° C. bath. The solution was degassed, then iPrMgCl (2M in THF, 1.93 L, 1.02 equivalents) was added over 40 min at a temperature of −21 to 1.5° C. The mixture was aged 30 min, cooled to −13° C. and allyl bromide (0.34 L, 1.04 equivalents) was added over 22 min at −13 to 9.7° C. The mixture was aged 1h at 14 to 20° C., quenched with water and acidified to pH 1.3 with 25 mL concentrated hydrochloric acid (HCl). Then 1.7 L acetic acid (EtOAc) was added and the organic layer was washed with 2×1.4 L water and 1.4 L brine. After drying over magnesium sulfate, the organic layer was concentrated to afford the olefin (III).

Step 2: Oxidation. The olefin (III) was diluted in 3.2 L of acetonitrile and 3.2 L water was added. The mixture was cooled to 16° C. and 497 g (1 equivalent) sodium periodate (NaIO$_4$) was added followed by 9.6 g (0.2 equivalent) of ruthenium chloride (RuCl$_3$) hydrate. The temperature gradually increased (up to 38° C.). An addiitional 3.5 equivalents of NaIO$_4$ was added over 2 h, while maintaining the temperature at 12–20° C. After 2 hours at 17° C., EtOAc was added and the mixture was agitated.

The mixture was filtered through a bed of Solka floc and transfer/rinsed with EtOAc. The organic layer was washed with 0.1 N HCl (1.3 L), saturated sodium thiosulfate (1.9 L), and brine (1.9 mL). The organic layer was concentrated by rotary evaporation and flushed with EtOAc (2×250 mL). Addiotional EtOAc (500 mL) was added and the mixture was heated to 50° C. to form a solution, which was filtered through Solka floc with EtOAc rinse. The brown filtrate was rotary evaporated to form a slurry and flushed with 2×500 mL hexanes then diluted with 500 mL hexanes. NMR showed ~14 vol % EtOAc/hexanes. The slurry was filtered (ML 600 mL) and rinsed with 200 mL 7% EtOAc/hexanes and 200 mL hexanes. The solids were dried for 2 days at ~35° C. to afford 2, 4, 5-trifluorphenylacetic acid.

While the invention has been described and illustrated with reference to certain particular embodiments thereof, various adaptations, changes, modifications, substitutions, deletions, or additions of procedures and protocols may be made without departing from the spirit and scope of the invention.

What is claimed is:

1. A process for the preparation of a compound of formula 3:

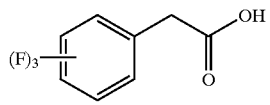

3 comprising contacting a compound of the formula 1:

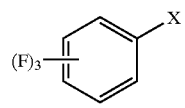

1 wherein X is a halogen selected from chlorine, bromine and iodine, with a magnesium compound and an allylating agent to produce a compound of formula 2,

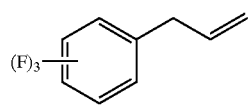

2 and reacting the compound of formula 2 with a metal catalyst and a co-oxidant to form a trifluorphenylacetic acid of formula 3.

2. A process in accordance with claim 1 wherein the compound of formula 1 is a 2,4,5-trifluorobenzene of the formula:

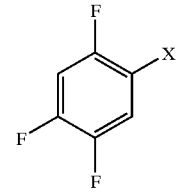

wherein X is a halogen selected from chlorine, bromine and iodine.

3. A process in accordance with claim 2 wherein the compound of formula 1 is 1-bromo-2,4,5-trifluorobenzene.

4. A process in accordance with claim 1 wherein the compound of formula 2 is 1-(2-propenyl)-2,4,5-trifluorobenzene.

5. A process in accordance with claim 1 wherein the compound of formula 3 is 2,4,5-trifluorophenylacetic acid.

6. A process in accordance with claim 1 whereby the allylating agent is allyl bromide.

7. A process in accordance with claim 1 wherein the metal catalyst of the reaction is ruthenium chloride.

8. A process in accordance with claim 1 wherein the co-oxidant of the reaction is sodium periodate.

9. A process in accordance with claim 1 wherein the reaction is carried out at about −20–40° C.

10. A process for the preparation of 2,4,5-trifluorophenylacetic acid of the formula III:

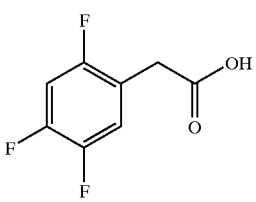

III comprising reacting 1-bromo-2,4,5-trifluorobenzene of the formula I:

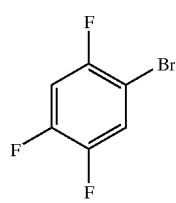

I with magnesium chloride and allyl bromide to form an olefin intermediate of the formula II:

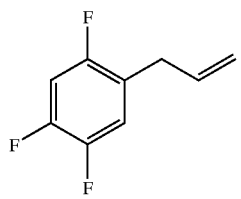 II
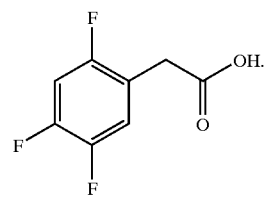 III
and reacting the compound of formula II with ruthenium chloride and sodium periodate to form 2,4,5-trifluorphenylacetic acid of the formula III:
* * * * *